United States Patent [19]

Brenden et al.

[11] Patent Number: 5,292,525
[45] Date of Patent: Mar. 8, 1994

[54] METHOD AND COMPOSITION FOR REMOVING AN ALGINATE FROM A CUTANEOUS SUBSTRATE

[75] Inventors: R. A. Brenden, Clayton; J. Burkey, Fenton; F. T. Kirchner, St. Charles, all of Mo.

[73] Assignee: Merck & Co., Inc., Rahway, N.J.

[21] Appl. No.: 961,003

[22] Filed: Oct. 14, 1992

[51] Int. Cl.$^5$ ............................................. A01N 59/26
[52] U.S. Cl. .................................. 424/601; 252/32.5; 252/DIG. 11; 602/49
[58] Field of Search ...... 424/601; 252/32.5, DIG. 11; 602/49; 134/38, 42

[56] References Cited

U.S. PATENT DOCUMENTS

| | | | |
|---|---|---|---|
| Re. 29,909 | 2/1979 | Kurtz | 252/89 R |
| 4,948,575 | 8/1990 | Cole et al. | 424/44 |
| 5,197,945 | 3/1993 | Cole et al. | 602/49 |

FOREIGN PATENT DOCUMENTS 8912471 12/1989 PCT Int'l Appl. .
9001954  3/1990 PCT Int'l Appl. .
 653341  5/1951 United Kingdom .

OTHER PUBLICATIONS

Couperwhite et al., "The Influence of EDTA on the Composition of Alginate Synthesized by *Azotobacter Vinelandii*", Arch. Microbiol. 97, 73-80 (1974).

*Primary Examiner*—Glennon H. Hollrah
*Assistant Examiner*—Deborah Lamblum
*Attorney, Agent, or Firm*—Richard S. Parr; Paul D. Matukaitis; Melvin Winokur

[57] ABSTRACT

The use of aqueous compositions containing at least one chelating agent in the removal of alginates from cutaneous substrates to which they are bound is disclosed. Such compositions, which may also contain physiological salts and non-ionic surfactants, are particularly useful in the removal of alginate wound dressings from human or animal wounds, skin, or cellular tissue.

8 Claims, 6 Drawing Sheets

METHOD AND COMPOSITION FOR REMOVING AN ALGINATE FROM A CUTANEOUS SUBSTRATE

BACKGROUND OF THE INVENTION

The present invention relates generally to the removal of an alginate from a cutaneous substrate using an aqueous solution of at least one chelating agent. While chelants have been used industrially to remove alginates from substrates such as floors and vessels, their use in the field of wound management is believed to be novel.

The instant chelant compositions are of particular benefit in the field of wound management, where alginate wound dressings are commonly used. In addition to chelating agents, these compositions may also contain physiological salts and one or more EO/PO-type surfactants. The preferred compositions of this invention are non-cytotoxic.

Alginate fibres have been known for some time as being useful in the preparation of surgical dressings. For example, United Kingdom Patent No. 653341 describes surgical dressings formed from fibres of calcium alginate. This reference recognizes that a failing of calcium alginate fibres is their relative insolubility in water or wound exudate matter. Bonniksen in GB-A-653341 therefore proposed that a proportion of the calcium ions in calcium alginate be replaced by sodium cations, since sodium alginate was known to be more soluble than calcium alginate. The resulting process has become known as "conversion" of calcium alginate to form a mixed salt alginate.

As used herein, the term "alginate" refers to any salt of alginic acid. In particular, the class of alginates includes but is not limited to, calcium, magnesium, sodium and potassium alginates, and mixtures thereof. Alginate wound dressings include any alginate-containing dressings used in the fields of human or animal wound management.

For example, EP 433354 discloses the use of mixed salt alginates in the manufacture of wound dressings. In such dressings, the mixed salt alginate forms the wound contact pad. U.K. 8815132 discloses the use of mixed alginate salt fibre dressings on skin wounds. KALTOSTAT ® is a highly absorbent alginate wound dressing which is commercially available from Calgon Vestal Laboratories.

If dry, alginate wound dressings are generally removed by simply soaking the dressing with saline for several minutes. Though this procedure tends to soften alginate dressings, subsequent removal of the dressing may still be difficult. By contrast, the instant chelant compositions solubilize or dissolve, at least to some extent, alginates, thereby facilitating removal of alginates from cutaneous substrates to which they are affixed. This method of removal is not known or suggested in the art.

As used herein, the term "chelating agent" refers to any compound having the ability to complex, solubilize or bind a base metal present in an alginate fiber, particularly a calcium, magnesium, sodium or potassium ion. As such, the term chelating agent as used herein is synonymous, inter alia, with the following terms: chelant, sequestrant, sequestering agent and complexing agent. In theory, any chelating agent which solubilizes an alginate can be used in the instant compositions.

As mentioned above, the instant compositions may contain one or more physiological salts and one or more surfactants in addition to the chelating agent. While copending and commonly assigned application U.S. patent application Ser. No. 446,276 discloses the use of aqueous compositions comprising physiological salts and EO/PO block copolymers in wound management, the presence of chelating agents is not disclosed. Exemplary of such compositions is the product SAF-CLENS ® which is commercially available from Calgon Vestal Laboratories.

Also, U.S. Pat. No. 29,909 to Kurtz discloses a method of cleansing wounds which utilizes aqueous detergent solutions of ethylene oxide (EO)/propylen oxide (PO) block copolymers. The block copolymers of Kurtz are commercially available as PLURONIC ® Polyols from BASF Kurtz discloses that his designated EO/PO polymers do not impair the ability of a wound being treated to resist infection. The claimed Kurtz wound cleansing compositions consist of an aqueous detergent solution of at least about 10% of an EO/PO block copolymer having an EO/PO ratio of at least 3:1 and a molecular weight of from about 5,000 to about 15,000.

A wound cleanser known as SHUR CLENS ®, which is commercially available from Calgon-Vestal Laboratories, represents a commercial embodiment of a wound cleansing composition disclosed by Kurtz.

DESCRIPTION OF THE FIGURES

FIG. 1 shows an untreated alginate pad. FIGS. 2-6 show alginate pads solubilized in accordance with the "chelation score" rating system of the instant examples.

SUMMARY OF THE INVENTION

Figure 1:
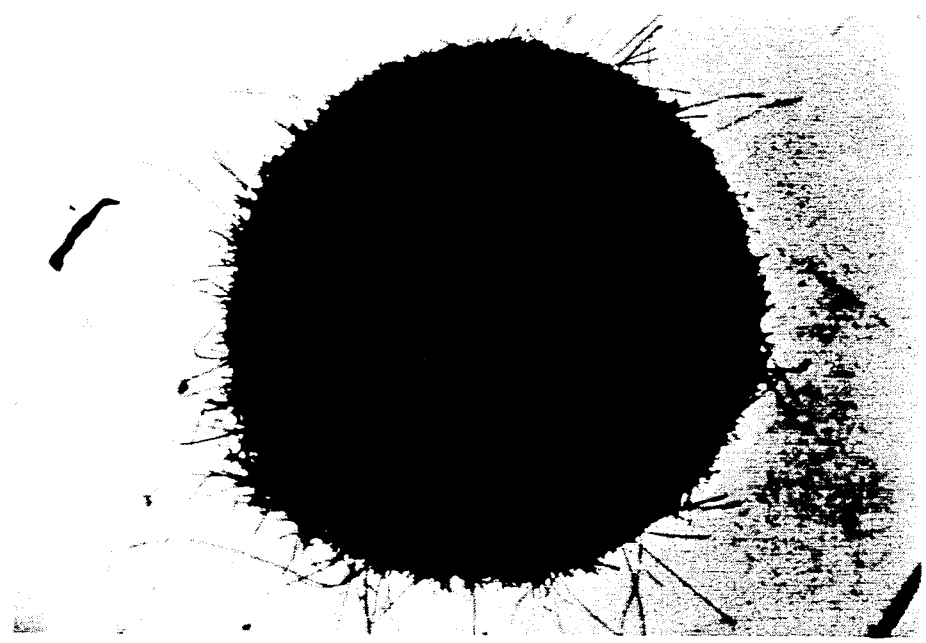
FIGS. 1-6 photographically demonstrate the impact of a chelant composition on alginate pads. More particularly.
Figure 2:
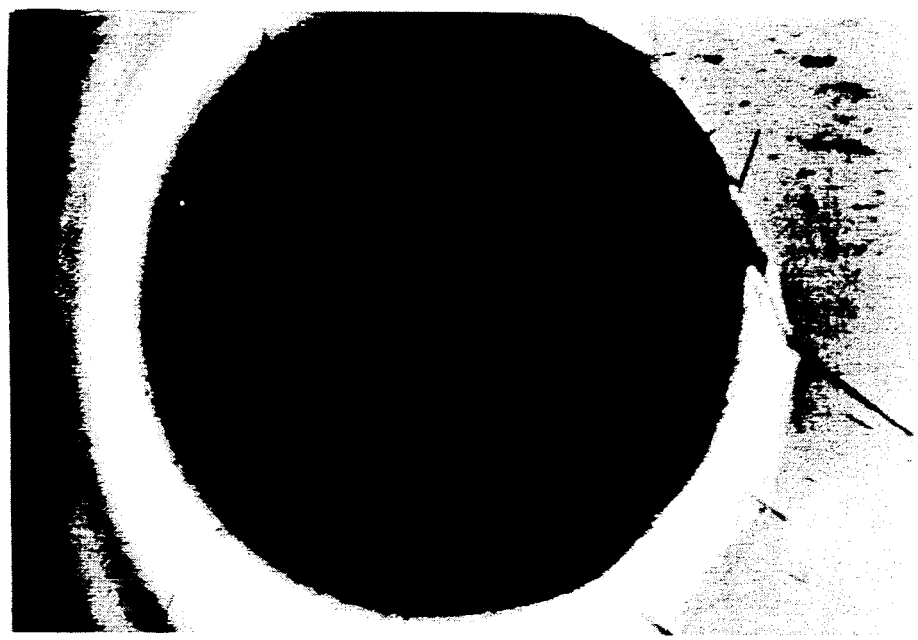
Figure 3:
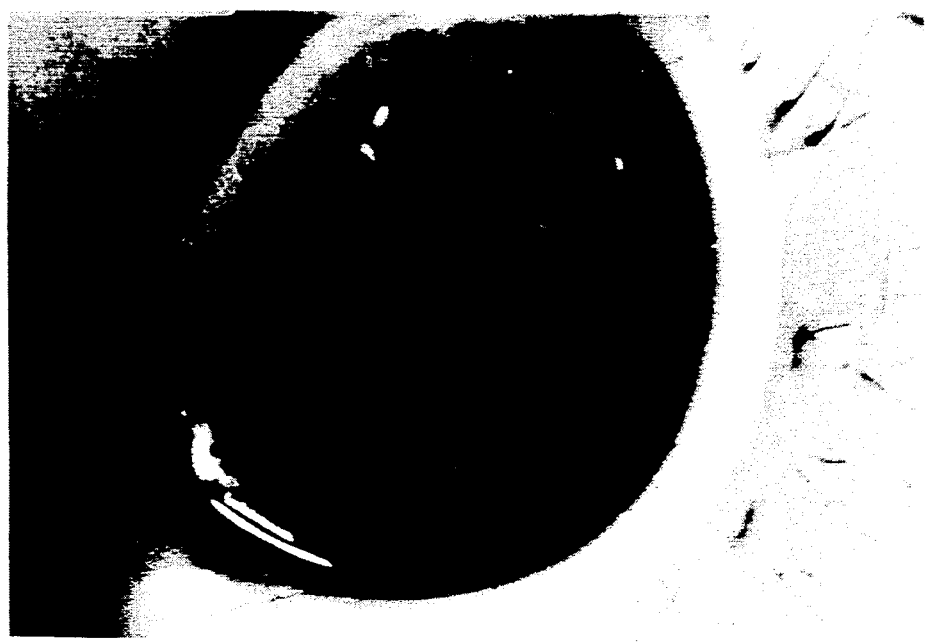
Figure 4:
Figure 5:
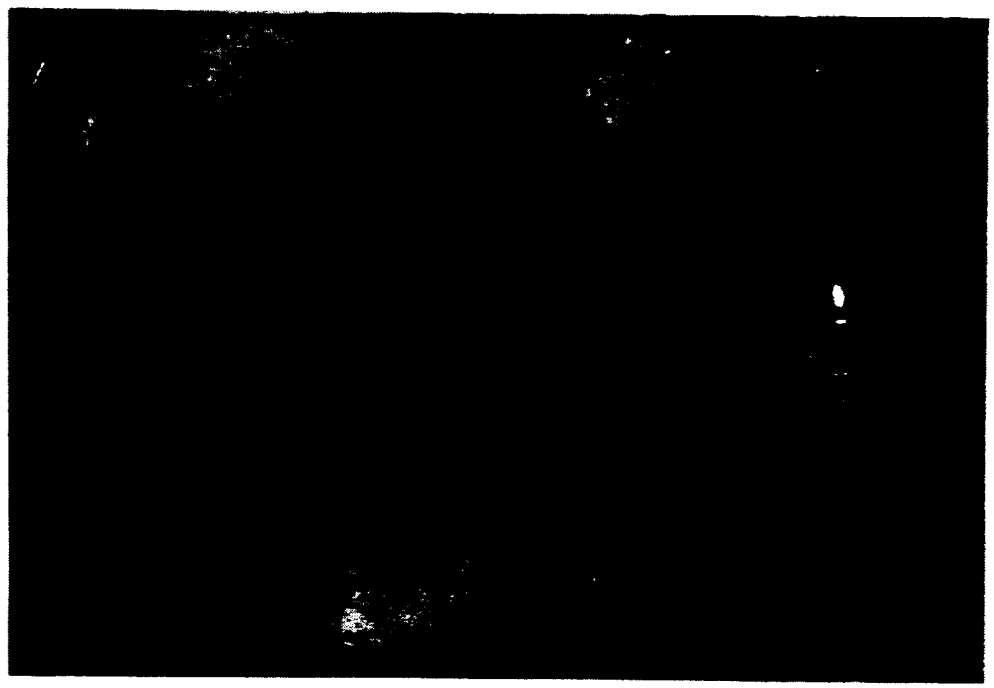
Figure 6:

In general terms, the instant invention relates to aqueous chelant compositions and to the use thereof in wound management to remove alginate dressings from cutaneous substrates. Thus, in its broadest sense, the present invention involves contacting a wet or dry alginate which is affixed to a cutaneous substrate with a chelant solution, thereby dissolving or solubilizing at least some portion of said alginate into the chelant solution and facilitating removal of the alginate from the cutaneous substrate to which it is affixed.

In the instant method, an effective amount of an aqueous chelant composition is applied by any convenient means to a wet or dry alginate wound dressing which is adhering to a cutaneous surface, such as human or animal skin, nail or wound tissue. As used herein, the term "effective amount" refers to that amount of a chelant composition necessary to solubilize a given alginate to the desired extent. Virtually any amount of a chelating solution will begin to solubilize and soften an alginate dressing. Thus, upon contact with one of the instant compositions, the alginate is partially or completely dissolved or solubilized, thereby facilitating removal. In a preferred embodiment, the alginate dressing is completely solubilized and flushed away, leaving a substantially clean cutaneous substrate.

In a more preferred embodiment of the instant invention, a non-cytotoxic alginate removal composition is used. Thus the instant invention also relates to the use of an effective amount for the above described purpose of a non-cytotoxic aqueous composition comprising: a) at least about 0.1%, by weight, of a non-cytotoxic chelating agent; b) optionally about 0.001 to about 2.0%, by weight, of a physiological salt; c) optionally, about 0.1 to about 40%, by weight, of a non-cytotoxic, non-ionic EO/PO-type surfactant; and d) the balance water; for the purpose of solubilizing, softening, facilitating the removal of and/or cleansing an alginate wound dressing from a human or animal cutaneous substrate in a non-cytotoxic way. Such compositions can generally be applied to an alginate dressing covering skin or wound tissue without causing substantial damage to the cellular tissue underlying the dressing. These preferred non-cytotoxic compositions are also claimed herein.

It is noteworthy that various components of wound management solutions may be toxic in a wound cleansing sense (that is, cytotoxic) even though they would be considered non-toxic by other standards of measurement, for instance, oral toxicity, eye irritation, and skin sensitivity. Thus, while a number of components used in wound management compositions, such as detergents, may be classified as non-toxic on the basis of various methodologies, they may unfortunately prove to be toxic in a wound healing sense in that they are cytotoxic.

Most commercial wound cleansers are intended for use as cleansing or irrigating solutions with minimal or short term exposure to tissues. Wound cleansers usually contain anionic or amphoteric surfactants in low concentrations to provide enhanced cleaning. However, these cleansers generally lyse or kill the tissue cells in in-vitro cell cultures, usually within fifteen minutes, and they generally do not effectively solubilize alginates. Though normal saline is commonly used as an irrigation fluid in the field of wound management, it has limited cleansing or solubilizing action relative to alginates. The preferred chelating compositions of this invention differ in that they solubilize alginates and can remain in contact with wounds for extended periods of time without causing substantial cytotoxicity. As used herein the term "non-toxic" and "non-cytotoxic" refers to components of alginate solubilizing compositions which do not cause substantial cytotoxicity as determined by the "Cytotoxicity Assay Protocol" described herein. Thus the preferred chelating agents of this invention are substantially non-cytotoxic, particularly in combination with at least one physiological salt.

DETAILED DESCRIPTION OF THE INVENTION

In general terms, the instant invention is directed to a method for the removal of an alginate from a cutaneous substrate, wherein said method comprises A) contacting said alginate with an effective amount of a composition which comprises:
(a) at least about 0.1 weight %, based on the weight of said composition, of at least one chelating agent; and
(b) the balance water; thereby solubilizing, to some extent, said alginate and facilitating its removal from said cutaneous substrate; and B) removing said alginate from said cutaneous substrate. Physiological salts and/or ethylene oxide/propylene oxide block copolymers can also be used in these compositions.

The instant invention is also directed to a method for softening and/or solubilizing an alginate wound dressing which comprises contacting said dressing with an effective amount of one of the above-described chelant compositions.

More particularly, the instant invention is directed to an improved method for the removal of an alginate dressing from wound, skin or cellular human or animal tissue, wherein the improvement comprises contacting said alginate with an effective amount of one of the above described compositions, thereby solubilizing said alginate to some extent and facilitating its removal from the tissue covered by said dressing. Preferably, the alginate is completely solubilized and the previously covered surface is then rinsed or flushed with said composition or with a conventional rinsing agent such as saline to cleanse and/or irrigate the underlying tissue. Alternatively, if the dressing is not completely solubilized, the remaining, softened dressing is removed by conventional means.

The instant invention is also directed to compositions comprising:
(a) at least about 0.1%, based on total composition weight, of a chelant selected from the group consisting of:
(i) organic acids selected from the group consisting of citric acid, acetic acid, ethylenediamine tetracetic acid, nitrilotriacetic acid, malonic acid tartaric acid, N-hydroxyethyl-ethylene diaminetriacetic acid, diethylenetriamine pentaacetic acid, trans-1,2, cyclohexamine diamine tetracetic acid, gluconic acid and salts thereof;
(ii) polyphosphates; and
(iii) anionic vinyl addition polymers containing at least about 30%, by weight, carboxylate functionality;
(b) about 0.001 to about 2.0%, based on total composition weight, of a physiological salt;
(c) optionally, an effective amount of a nonionic, water soluble EO/PO block copolymer; and
(d) the balance water.

The instant invention is further directed to a method for removing alginates from cutaneous substrates in a non-cytotoxic manner by the use of preferred chelant compositions which have been found to be substantially non-cytotoxic. These compositions comprise: a) at least about 0.1%, based on the weight of said composition, of at least one non-cytotoxic chelating agent; b) optionally, about 0.001 to about 2.0%, based on the weight of said composition, of at least one physiological salt; c) optionally, about 0.1 to about 40%, based on the weight of said composition, of at least one non-cytotoxic ethylenoxide/propylene oxide-type surfactant polymer; and d) the balance water. A non-cytotoxic method for removing alginate wound dressings from cutaneous substrates using these non-cytotoxic compositions is also claimed.

Generally speaking, the solubilizing/alginate removal compositions described herein may be prepared by simply dissolving at least one chelant in water as component (a). The chelant can be present in an amount of from about 0.1 weight % of said composition up to its solubility limit. Deionized (DI) or distilled water is the preferred solvent.

In theory, any chelant which solubilizes a counter ion found in an alginate wound dressing can be used. Such chelants include, but are not limited to a) organic acids selected from the group consisting of citric acid, acetic acid, ethylenediamine tetracetic acid (EDTA), nitrilotriacetic acid (NTA), malonic acid, tartaric acid, N-hydroxyethyl-ethylene diaminetriacetic acid (HEEDTA), diethylenetriamine pentaacetic acid, trans-1,2, cyclohexamine diamine tetraacetic acid, gluconic acid and salts thereof, especially sodium salts; b) chelating polyphosphates; and c) polymers selected from the group consisting of water-soluble anionic vinyl addition polymers which are generally recognized to function as sequestering agents, such as those which contain at least about 30%, by weight, of carboxylate functionality and have a molecular weight within the range of about 500–500,000. Examples of such polymers include those containing acrylic acid or methacrylic acid moieties, and salts thereof. Hydrolyzed polycrylamides also have sequestering properties.

The preferred chelants relative to this invention are polyphosphates which are believed to be generally superior to the organic surfactants from a toxicity perspective. While the instant inventors believe that virtually any water soluble polyphosphate having the ability to chelate alginate counter ions can be used as component (a) in the compositions of the present invention, preferred polyphosphates are "molecularly dehydrated phosphates", by which is meant any phosphate which can be considered as derived from a monobasic or dibasic orthophosphate or from orthophosphoric acid, or from a mixture of any two of these by elimination of water of constitution therefrom. Examples of such phosphates include alkaline metal tripolyphosphates, pyrophosphates, and metaphosphates, which are often designated as hexametaphosphates.

While it is believed that any molecularly dehydrated phosphate may be employed, it is preferred to use those which have a molar ratio of alkaline metal to phosphorous methoxide from about 0.9:1 to about 2:1, the latter being the alkaline metal pyrophosphate. While it is preferred to use the metaphosphates, pyrophosphates, or polyphosphates of sodium, because they are the least expensive and most readily available, it is also believed to be possible to use the molecularly dehydrated phosphates of other metals such as potassium, lithium, cesium, or rhobidium or the ammonium molecularly dehydrated phosphates, which in many instances are classified as being alkaline metal phosphates, or the alkaline earth metal molecularly dehydrated phosphates such as those having calcium, barium, or strontium, or mixtures of alkaline metal and alkaline earth molecularly dehydrated phosphates.

The most preferred water soluble phosphates are sodium hexametaphosphate (SHMP), such as "Calgon" which is available from Calgon Corporation, Pittsburgh, PA, and which may be described as 1.1 $NaO_2$:1-$P_2O_5$; tetrasodium pyrophosphate (TSPP); and sodium tripolyphosphate (STP).

Generally, the chelant should comprise at least about 0.1%, by weight, of the instant composition. Preferably, the chelant should comprise about 0.1% up to its solubility limit to a maximum of about 15%, based on the total weight of the instant composition.

A preferred embodiment of this invention relates to the use of an effective amount of a composition comprising: a) at least about 0.1%, by weight of the composition, of a water soluble polyphosphate selected from the group consisting of sodium hexametaphosphate, tetrasodium pyrophosphate and sodium tripolyphosphate; and b) the balance water; for the purpose of solubilizing an alginate wound dressing. These preferred polyphosphate compositions are generally believed to be less cytotoxic than compositions containing either the organic chelating agents or the polymeric sequestrants mentioned above.

Additionally, these preferred compositions may comprise from about 0.001% to about 2.0%, by weight of the composition, of at least one physiological salt and, optionally, an EO/PO-type surfactant polymer. The concentration of the EO/PO polymer in the water, if used, may vary according to the strength of the detergency sought and the desired viscosity. If detergency is desired, the EO/PO surfactant polymer must be present at a sufficient concentration to effect cleansing of the wound, skin or cellular tissue being treated. In general, aqueous solutions containing up to about 20% active polymer can be used. Preferred EO/PO surfactant polymers are those which are substantially non-cytotoxic, such as an EO/PO block copolymer having an EO/PO ratio of at least 3:1 and a molecular weight of from about 5,000 to about 15,000. Exemplary of such surfactants is PLURONIC® F-68, which is commercially available from BASF.

Any physiological salt can be used. As used herein, the term "physiological salt" refers to any salt which, when in aqueous solution at a concentration, by weight, of less than or equal to about 2.0%, does not substantially alter the function or integrity of the cells of a wound in contact with the salt solution. Examples of physiological salts include alkaline and alkaline earth metal chlorides, phosphates and sulfates. Preferred physiological salts include KCl, NaCl, $MgCl_2$, $CaCl_2$, and mixtures thereof. The most preferred physiological salt is NaCl. Physiological salts are believed to generally reduce the cytotoxicity of the chelants used in the instant compositions and method.

Preferably, the physiological salt concentration in the instant compositions will range from about 0.1 to 1.75 weight %, most preferably from about 0.2 to 1.3 weight %, based on total composition weight. In no instance, however, should the salt concentration exceed about 2.0%, by weight, of the total composition. At higher concentrations, the salt itself is generally toxic to wound tissues.

The surfactant polymers, if used, are block copolymers of ethylene oxide (EO) and propylene oxide (PO).

An effective amount, preferably about 0.1% to about 40%, by weight of the composition, of at least one nonionic, water soluble surfactant polymer selected from the group of ethylene oxide/propylene oxide block copolymers defined as:

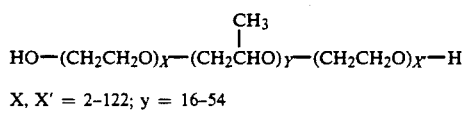

$$HO-(CH_2CH_2O)_X-(CH_2\overset{\overset{\displaystyle CH_3}{|}}{C}HO)_Y-(CH_2CH_2O)_{X'}-H \qquad (I)$$

X, X' = 2–122; y = 16–54

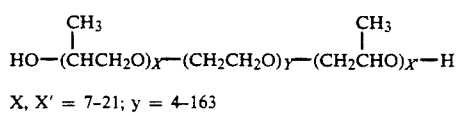

$$HO-(\overset{\overset{\displaystyle CH_3}{|}}{C}HCH_2O)_X-(CH_2CH_2O)_Y-(CH_2\overset{\overset{\displaystyle CH_3}{|}}{C}HO)_{X'}-H \qquad (II)$$

X, X' = 7–21; y = 4–163

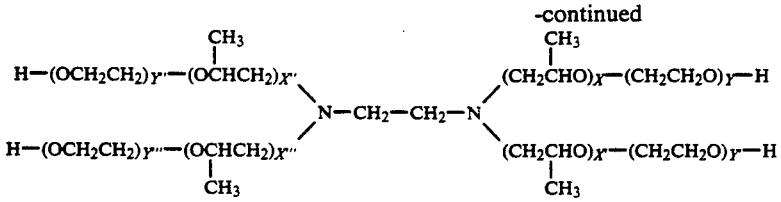
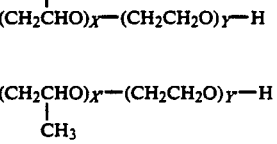

X, X', X" X'" = 2-122; y, y', y", y'" = 2-32 or

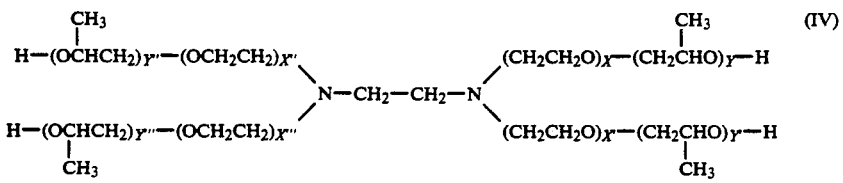
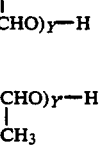

X, X', X", X'" = 2-122; y, y", y'", = 2-32

Preferably, suitable polymers include I) polymers which comprise poly(oxyethylene) groups at both ends of poly(oxypropylene) chain; II) polymers which comprise poly(oxypropylene) groups at both ends of a poly(oxyethylene) chain; III) polymers which comprise PO-EO capped ethylene diamines; and IV) polymers which comprise EO-PO capped ethylenediamines. Examples of such copolymer surfactants include products sold under the tradenames PLURONIC (Class I), PLURONIC ® (Class II), TETRONIC (Class II), and TETRONIC R (Class IV), which are commercially available from BASF Corporation. Methods for preparing such polymers are well known in the art.

The most preferred surfactant polymers are the polymers of type II), and the most preferred surfactant polymers are those of type II) wherein the EO/PO molar ratio is greater than 3:1. Such polymers are believed to be substantially non-cytotoxic.

If used, the EO/PO polymer preferably comprises about 0.1% to about 40% by weight of the instant compositions, more preferably about 0.1% to about 20% and most preferably about 0.5 to about 5%.

These surfactants must be water-soluble at use concentrations, and preferably exhibit a solubility in water of greater than about 10 grams per 100 ml.

If desired, the instant compositions may also include other materials commonly employed in wound cleansing solutions. For example, effective amounts for the purpose of preservatives, dyes, emollients, perfumes, sugars, proteins, vitamins, minerals, glycols and/or alcohols can be added. Additionally, any known antiseptic or antimicrobial can optionally be added. Such antiseptic or antimicrobial agents include, but are not limited to, ethyl alcohol, benzalkonium chloride, chlorhexidine gluconate, iodine, iodophors such as polyvinylpyrrolidone/iodine, and the like.

The balance of the instant compositions is water. Of course, relatively pure water, for example, USP purified water, is preferred.

Any known technique for contacting an alginate wound dressing with the instant compositions may be employed, including but not limited to swabbing or scrubbing with gauze, a sponge, surgical cotton and the like moistened with the instant solubilizing solution, soaking of the wound dressing in the instant composition, hypodermic flushing of the wound dressing using the instant composition and pouring or spraying the instant composition onto an alginate wound dressing.

The key to the above described inventions is that effective amounts of the instant compositions solubilize alginate wound dressings, thereby allowing substantially complete removal of such dressings from wounds without substantial irritation to the wound or cellular tissue underlying the dressing.

EXAMPLES

The following examples are intended to further demonstrate the instant invention. They are not intended to limit the invention in any way.

SOLUBILIZATION TEST PROTOCOL

The following procedure was used to evaluate various chelant compositions:

1) Using a paper punch, uniform disks of various alginate fiber pads were made. Ten (10) of these disks were weighed to determine an average weight/alginate disk.
2) The disks were placed, one per well, in a 24 well tissue culture dish.
3) 100 μl of chelating solution were added per ~0.0050 grams of alginate fiber, and the alginate fiber pads were allowed to soak for thirty (30) seconds.
4) After thirty seconds, the alginate fibers were examined macroscopically and microscopically at a magnification of 10× using a stereo microscope. Ratings were made using the following scoring system:

| Observation | | Chelation Score |
|---|---|---|
| 1. | Partial gel stiff and wet. No solubilizing of fiber | 1 |
| 2. | Partial gel, slightly soft. Still has integrity. | 2 |
| 3. | Partially solubilized, can be torn. | 3 |
| 4 | Viscous liquid, gel mostly solubilized. | 4 |
| 5. | Liquid for the most part. | 5 |

Use of a "+" means that the numerical designator is similar to the above descriptions, but the more it is manipulated, the more it acts like the next level up.

Photographs demonstrating these classes are shown herein as FIGS. 1-6. FIG. 1 shows an untreated alginate pad.

The compounds tested are listed below:

List of Tested Compounds 0.1% Sodium Hexametaphosphate, 2% 10R-5, in saline (Sodium Polymetaphosphate)
0.1% Sodium Hexametaphosphate in saline
0.1% Sodium Hexametaphosphate in water
1.0% Sodium Hexametaphosphate, 2% 10R-5, in saline
1.0% Sodium Hexametaphosphate in saline
1.0% Sodium Hexametaphosphate in water
5% Sodium Hexametaphosphate, 2% 10R-5, in saline
5% Sodium Hexametaphosphate in saline
5% Sodium Hexametaphosphate in water
10% Sodium Hexametaphosphate, 2% 10R-5, in saline
10% Sodium Hexametaphosphate in saline
10% Sodium Hexametaphosphate in water
15% Sodium Hexametaphosphate, 2% 10R-5, in saline
15% Sodium Hexametaphosphate in saline
15% Sodium Hexametaphosphate in water
5% EDTA acid in saline (Ethylenediaminetetraacetic acid)
5% Malonic Acid in saline (Propanedioic acid)
5% Citric Acid in saline
5% Acetic Acid in saline
5% Tartaric Acid in saline (2,3-Dihydroxybutanedioic acid)
5% Tetrasodium Pyrophosphate in saline (TSPP)
5% Sodium Tripolyphosphate in saline (STP)
5% HEEDTA in saline (N-hydroxyethyl-ethylenediaminetriacetic acid)
5% Sodium Gluconate in saline
5% Sequestrene Na3 in saline (Trisodium Ethylenediaminetetraacetic acid)
5% Sequestrene Na2 in saline (Edetate Disodium or Ethylenediaminetetraacetic acid disodium salt)
5% CHEL DTPA in saline (Diethylenetriaminepentaacetic Acid)
5% CDTA in saline (trans-1,2-cyclohexanediaminetetra acetic acid)
Saline
2% Pluronic 10R-5 in saline
0.05% Sodium Lauryl Sulfate in saline
Sterile distilled water
Phosphate Buffered Saline
0.1% Sodium Lauryl Sulfate in saline

CYTOTOXICITY ASSAY PROTOCOL

The cytotoxicities of various components of the instant compositions were measured according to the following procedure:

1) 6 well tissue culture plates were seeded with $4.5 \times 10^4$ L929 fibroblast cells per well. The cells were incubated for 5 days until cells form a confluent monolayer (i.e., layer at least 1 cell thick) on bottom of plate.
2) One at a time, the plates were inverted over a plastic beaker to remove the media. Any remaining media was removed by blotting the edges of the inverted plate on lint free paper towels.
3) 1 ml of sample was added to each of two wells with a plastic pipet dropper, taking care not to damage the monolayer.
4) The plates were placed in the 32° C. chamber of an incubator (non $CO_2$) for five minutes.
5) Just prior to step 6, solutions of fluorescein diacetate were prepared, as described below.
6) The plates were removed from the incubator at the end of 5 minutes, and they were inverted and blotted as in step 1 to remove the test substance.
7) 1 ml of the fluorescein diacetate solution was added to each well. The plates were placed in the 4° C. refrigerator for 15 to 20 minutes.
8) The plates were viewed using an inverted microscope with brightfield and fluorescent settings. Cells in the same field were viewed by fluorescent light and brightfield microscopy to determine the percentage of total cells fluorescing. Several fields per well were viewed. An average percentage of fluorescent cells from two wells of a sample was recorded. Dull or faded fluorescence was documented by notations to qualify the percent fluorescence recorded.

Interpretation

Evaluations of 70-100% fluorescence are considered non-toxic. Evaluations of 40-60% fluorescence are considered moderately cytotoxic. Evaluations of 0-30% fluorescence are considered cytotoxic. In general, low percentages of fluorescence are taken as evidence of cytotoxicity in this assay; no fluorescent cells visible is interpreted as complete cytotoxicity.

The fluorescent diacetate stock solution was prepared by adding powdered dye to acetone at a concentration of 5 mg/ml (0.005 gms/ml of acetone) in a glass tube. Stock solutions were made fresh on the day of the test and the unused portion was discarded at the end of the day. The stock solutions were protected from light by wrapping the tube in aluminum foil.

The needed amount of stock solution was added to an 0.85% (1×) Phosphate Buffered Saline (PBS) to make a final dye concentration 0.002%. This ratio is 0.1 stock solution per 25 ml of PBS. The dye falls out of solution over time (approximately 1 hour) since the dye is not highly water soluble.

Results of these tests are shown in Tables 1-3, below.

TABLE 1

Concentration Range
Chelator: Sodium Hexametaphosphate

| Chelator | Saline | 2% Pluronic 10R-5 | Cytotoxicity Test: % Viability 5 minutes | Solubilization Test:* Chelation Score 30 seconds |
|---|---|---|---|---|
| 0.1% | Yes | Yes | 100 | 1 |
| 0.1% | Yes | No | 95 | 1 |
| 0.1% | No | No | 70 | 1 |
| 1.0% | Yes | Yes | 100 | 1 |
| 1.0% | Yes | No | 100 | 1 |
| 1.0% | No | No | 95 | 2 |
| 5% | Yes | Yes | 100 | 3 |
| 5% | Yes | No | 100 | 4 |
| 5% | No | No | 100 | 4 |
| 10% | Yes | Yes | 100 | 4 |
| 10% | Yes | No | 95 | 5 |
| 10% | No | No | 95 | 5 |
| 15% | Yes | Yes | 100 | 5 |
| 15% | Yes | No | 95 | 5 |
| 15% | No | No | 100 | 5 |

*Scoring system:
1 Partial gel, stiff and wet. No solubilizing of fiber.
2 Partial gel, slightly soft. Still has integrity.
3 Partially solubilized, can be torn.
4 Viscous liquid, gel mostly solubilized.
5 Liquid for the most part.
+ Looks like the stated level, but the more it is manipulated the more it acts like the next level up.

TABLE 2

Class of Chelators
Chelator concentration: 5% in saline

| Chelator | Cytotoxicity Test: % Viability 5 minutes | Solubilization Test:* Chelation Score 30 seconds |
|---|---|---|
| Sodium Hexametaphosphate | 100 | 4 |

TABLE 2-continued

Class of Chelators
Chelator concentration: 5% in saline

| Chelator | Cytotoxicity Test: % Viability 5 minutes | Solubilization Test:* Chelation Score 30 seconds |
|---|---|---|
| Sodium Tripolyphosphate | 95 | 4 |
| Tetrasodium Pyrophosphate | 95 | 3+ |
| Sequestrene Na3 | 95 | 3+ |
| Sodium Gluconate | 100 | 2 |
| Sequestrene Na2 | 100 | 2 |
| Citric Acid | 0 | 2 |
| HEEDTA | 0 | 2 |
| Tartaric Acid | 0 | 1 |
| EDTA acid | 0 | 1 |
| Malonic Acid | 0 | 1 |
| Acetic Acid | 0 | 1 |
| CHEL DTPA | 0 | 1 |
| CDTA | 0 | 1 |
| ph adjusted | | |
| Tartaric Acid, pH 7 | 100 | 5 |
| Citric Acid, pH 7 | 100 | 4 |
| EDTA Acid, pH 7 | 100 | 3 |
| Malonic Acid, pH 7 | 100 | 2 |
| Acetic Acid, pH 7 | 100 | 2 |
| HEEDTA, pH 7 | 100 | 2 |
| CHEL DTPA, pH 7 | 100 | 2 |
| CDTA, pH 7 | 95 | 2 |

*Scoring system:
1 Partial gel, stiff and wet. No solubilizing of fiber.
2 Partial gel, slightly soft. Still has integrity.
3 Partially solubilized, can be torn.
4 Viscous liquid, gel mostly solubilized.
5 Liquid for the most part.
+ Looks like the stated level, but the more it is manipulated the more it acts like the next level up.

TABLE 3

Class of Alginates
Chelator concentration: 5% in saline
A) Sodium Hexametataphosphate
B) Sodium Tripolyphosphate
C) EDTA, pH adjusted to 7.0
Solubilization test: Chelation score, 30 second exposure*

| Alginates | Chelators A | B | C |
|---|---|---|---|
| Fiber Dressings | Ca:Na | | |
| Kaltostat | 80:20 | 3+ | 4 | 3+ |
| Algiderm | ... | 3 | 3+ | 2+ |
| Algosterile | ... | 3 | 3+ | 2+ |
| Fortex | 80:20 | 4 | 4+ | 3+ |
| Algistat | 99:1 | 3 | 3+ | 2 |
| Sorbsan | 96:4 | 3+ | 5 | 3+ |
| Powders | | | | |
| Kelmar (potassium alginate) | | 3 | 3 | 1 |
| Calcium Alginate | | 2 | 2 | 2 |
| Calcium/Magnesium Alginate | | 2 | 2 | 2 |

*Scoring system:
Dressings:
1 Partial gel, stiff and wet. No solubilizing of fiber.
2 Partial gel, slightly soft. Still has integrity.
3 Partially solubilized, can be torn.
4 Viscous liquid, gel mostly solubilized.
5 Liquid for the most part.
+ Looks like the stated level, but the more it is manipulated the more it acts like the next level up.
Powders:
1 Undissolved powder.
2 Large clumps, mostly undissolved.
3 Small clumps, some dissolved.
4 Mostly liquid
5 All liquid

What we claim is:

1. A method for removing an alginate from a cutaneous substrate which comprises: A) contacting said alginate with an effective amount of a chelant solution which comprises a) at least about 0.1 weight %, based on the weight of said composition, of a chelant; and b) the balance water; and B) removing said alginate from said cutaneous substrate.

2. The method of claim 1, wherein said chelant is a polyphosphate.

3. The method of claim 2, wherein said composition additionally comprises:
  a) about 0.001 to about 2%, based on the weight of said composition, of at least one physiological salt; and
  b) optionally, about 0.1 to about 40%, based on the weight of said composition, of a nonionic, water soluble EO/PO block copolymer.

4. The method of claim 3 wherein said physiological salt is selected from the group consisting of alkaline and alkaline earth metal chlorides, phosphates and sulfates and wherein said chelant is selected from the group consisting of sodium hexametaphosphate, tetrasodium pyrophosphate and sodium tripolyphosphate.

5. The method of claim 4 wherein said composition comprises about 0.1 to about 40% by weight of a water soluble EO/PO block copolymer having an EO/PO ratio of at least 3:1 and a molecular weight of from about 5,000 to about 15,000.

6. In an improved method for the removal of an alginate dressing from wound, skin or cellular human or animal tissue, the improvement which comprises contacting said alginate dressing with an effective amount of a composition which comprises: a) at least about 0.1%, based on the weight of said composition, of a chelant; and b) the balance water.

7. The method of claim 6, wherein said chelant is a polyphosphate.

8. The method of claim 7, wherein said polyphosphate is selected from the group consisting of sodium hexametaphosphate, tetrasodium pyrophosphate and sodium tripolyphosphate.

* * * * *